United States Patent [19]
Pamukcu et al.

[11] Patent Number: 5,958,982
[45] Date of Patent: Sep. 28, 1999

[54] METHOD FOR TREATING PATIENTS WITH SARCOIDOSIS BY ADMINISTERING SUBSTITUTED SULFONYL INDENYL ACETIC ACIDS, ESTERS AND ALCOHOLS

[75] Inventors: Rifat Pamukcu, Spring House; Gary Piazza, Doylestown, both of Pa.; Ewa Skopinska-Rozewska, Warsaw, Poland

[73] Assignee: Cell Pathways, Inc., Horsham, Pa.

[21] Appl. No.: 09/062,604

[22] Filed: Apr. 17, 1998

[51] Int. Cl.⁶ ................................................. A61K 31/19
[52] U.S. Cl. ...................... 514/570; 514/618; 514/702; 514/239.5
[58] Field of Search .................. 514/570, 618, 514/702, 239.5

[56] References Cited

U.S. PATENT DOCUMENTS

| | | |
|---|---|---|
| 4,393,063 | 7/1983 | Moncada . |
| 4,751,224 | 6/1988 | Agarwal et al. . |
| 5,011,843 | 4/1991 | Shell . |
| 5,401,754 | 3/1995 | Fujioka et al. . |
| 5,401,774 | 3/1995 | Pamukcu et al. . |
| 5,500,230 | 3/1996 | Nathanson . |

FOREIGN PATENT DOCUMENTS

| | | |
|---|---|---|
| 59-229468 | 5/1986 | Japan . |

OTHER PUBLICATIONS

Menashi et al., The extracellular matrix produced by bovine corneal endothelial cells contains progelatinase A; FEBS Letters, 361 pp. 61–64 (1995).

Volpert et al., Captopril Inhibits Angiogenesis and Slows the Growth of Experimental Tumors in Rats; J. Clin. Invest., vol. 98, No. 3, pp. 671–679 (Aug., 1996).

Isner, Jeffrey, The Role of Angiogenic Cytokines in Cardiovascular Disease; Clinical Immunology and Immunopathology, vol. 80, pp. S82–S91 (1996).

Sakamoto et al., Effect of Intravitreal Administration of Indomethacin on Experimental Subretinal Neovascularization in the Subhuman Primate; Arch Ophthalmol, vol. 113, pp. 222–226, (Feb. 1995).

Thölen et al., Die Behandlung der altersabhängigen Makuladegeneration mit Interferon–α–2a; Opthalmologe, vol. 90, pp. 279–282, (1993).

Clements et al., Anti–glycated albumin therapy ameliorates early retinal microvascular pathology in db/db mice; J Diabetes Complications, vol. 12(1), pp. 28–33 (Jan. 1998).

Vialettes et al., Perspectives D'Avenir Dans Le Traitement De La Retinopathie Diabetique; Diabete & Metabolisme, vol. 20, pp.229–234 (1994).

Skopinska–Rozewska et al., Abstract, Inhibition of Angiogenesis by Sulindac and its Sulfone Metabolite (FGN–1): A Potential Mechanism For Their Antineoplastic Properties; Interscience World Conference on Inflammation, Antirheumatics, Analgesics, Immunomodulators; Geneva, Switzerland. May 19–21, 1997.

*Primary Examiner*—James H. Reamer
*Attorney, Agent, or Firm*—Robert W. Stevenson

[57] ABSTRACT

Substituted indenyl sulfonyl acetic acids, esters and alcohols are useful in the treatment of sarcoidosis.

7 Claims, No Drawings

METHOD FOR TREATING PATIENTS WITH SARCOIDOSIS BY ADMINISTERING SUBSTITUTED SULFONYL INDENYL ACETIC ACIDS, ESTERS AND ALCOHOLS

BACKGROUND OF THE INVENTION

This invention relates to methods for treating sarcoidosis.

Sarcoidosis is a chronic lung disease of unknown etiology, which is believed to occur when the body's immune system overreacts to an unknown agent. Some authors have noted an association with HLA types B8 and B27 with various manifestations of the disease suggesting that genetic factors may be involved.

It is often described as incidentall finding as hilar adenopathy on a routine chest x-ray of an asymptomatic individual. The most common clinical findings of sarcoidosis is cough, followed by dyspnea, wheezing and hemoptysis. Auscultation of the lungs is usually unremarkable unless extensive fibrosis is present. Other organs may be involved, with granulomas found in the liver, heart, spleen and bone marrow in nearly half the cases. Eye, skin and salivary glands are involved in about one-third of the cases. Hypercalcemia and hypercalciurea occur in 20–30% of patients and may occasionally result in urolithiasis.

The clinical course is benign in most cases. Fortunately, nearly 70 percent of the afflicted patients will experience a remission. However, about 50 percent of patients have some permanent residual organ damage, and 20–25 percent of the patients have some abnormality pulmonary function. More disturbingly, up to 10% develop progressive fibrosis; and 5 percent of people with sarcoidosis die. Sarcoidosis that involves the heart is the cause of death in 50% of cases.

The current treatment for sarcoidosis starts with steroids. However, in intractable cases, other immunosuppressive therapies have been tried with variable success. Steroids have side effects, and long-term use can result in resistance to the treatment. Stronger immunosuppressive agents can be used, but they also have undesirable effects since an impaired immune system is the main effect.

Accordingly improved therapies for sarcoidosis are needed.

SUMMARY OF THE INVENTION

This invention is an improved therapy for sarcoidosis wherein an oral or topical application of compounds within the scope of Formula I below is administered to a patient in need of such treatment.

Such compositions have fewer side effects than conventional topical or oral therapies for sarcoidosis, and as such can be tolerated for longer-term administration than currently available medicaments.

DETAILED DESCRIPTION OF THE PREFERRED EMBODIMENTS

Compounds useful in the therapeutic methods of this invention include those of Formula I:

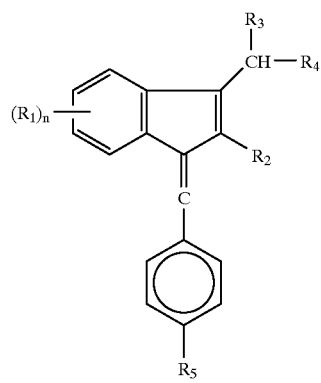

wherein $R_1$ is independently selected in each instance from the group consisting of hydrogen, halogen, lower alkoxy, hydroxy, lower alkyl, lower alkyl mercapto, lower alkylsulfonyl, lower alkylamino, di-lower alkyl amino, amino, nitro, nitrile, lower alkyl carboxylate, —$CO_2H$, and sulfonamido;

$R_2$ is selected from the group consisting of hydrogen and lower alkyl;

$R_3$ is selected from the group consisting of hydrogen, lower alkyl, hydroxy, and amino;

$R_4$ is selected from the group consisting of —COM and $CH_2OH$ wherein M is selected dialkylamino, N-morpholino, hydroxyalkylamino, polyhydroxyamino, dialkylaminoalkylamino, aminoalklyamino, and the group OMe, wherein Me is a cation;

$R_5$ is an alkyl sulfonyl; and n is an integer from 0 to four.

As explained above, this invention relates to a method of treating sarcoidosis by administering to an afflicted patient a therapeutically effective amount of a compound of Formula I above.

Preferred compounds within the scope of Formula I include those wherein $R_1$ is halogen; n is 1; $R_2$ is lower alkyl; M is hydroxy; and $R_3$ is hydrogen or lower alkyl. Most preferred compounds useful in therapeutic methods of this invention include those wherein $R_1$ is 5-fluoro; n is 1; $R_2$ is methyl; M is hydroxy; and $R_3$ is hydrogen.

As used herein, the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "lower alkyl carboxylate" refers to a carboxylate group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enaniomers may be synthesized from chiral starting materials, or the racemates can be resolved by conventional procedures that are well known in the art of chemistry such as chiral chromatography, fractional crystallization of diastereomeric salts and the like.

Compounds of Formula I also can exist as geometrical isomers (Z and E); the Z isomer is preferred.

Compounds useful in the practice of this invention may be formulated into pharmaceutical compositions together with pharmaceutically acceptable carriers for oral administration in solid or liquid form, or for rectal, intravenous, intramuscular, subcutaneous, transdermal, and topical, the most preferrred being oral.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds useful in the practice of this invention, excipients such as cocoa butter or a suppository wax, or gel. Pharmaceutically acceptable carriers for intraveneous administration include solutions containing pharmaceutically acceptable salts or sugars. Pharmaceutically acceptable carriers for intramuscular or subcutaneous injection include pharmaceutically acceptable salts, oils or sugars.

When used in its acid form, a compound useful in the practice of his invention can be employed in the form of a pharmaceutically acceptable salt of the acid. For example, sodium or potassium salts can be obtained by neutralizing with an equivalent base (alkali) metal hydroxide, mesylate of tosylate. When the active chemical is a base, it can be used as an acceptable formulation by neutralizing it with a suitable acid such as hydrochloric acid. Carriers such as solvents, water, buffers, alkanols, cyclodextrans and aralkanols can be used. Other auxiliary, non-toxic agents may be included, for example, polyethylene glycols, antimicrobial agents and wetting agents.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve activity in accordance with the desired method of administration (i.e., oral, rectal, or topical). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

Examples 1–3 illustrate compounds useful in the practice of the claimed invention.

EXAMPLE 1

α-(1-p-Methylsulfonylbenzylidene)-2-Methyl-5-Fluoro-3-Indeny-1-Acetic Acid (A) p-Fluoro-α-methylcinnamic acid.

p-Fluorobenzaldehyde (200 g., 1.61 mole), propionic anhydride (3.5 g., 2.42 mole) and sodium propionate (155 g., 1.61 mole) are mixed in a 1 liter, three-necked flask flushed with nitrogen. The mixture is heated gradually in an oil-bath to 140° C. After 20 hours, the flask is cooled to 100° C. and poured into 8 l. of water. The precipitate is dissolved by adding potassium hydroxide (302 g) in 2.1 of water. The aqueous solution is extracted with ether, and the ether extracts are washed with potassium hydroxide solution. The combined aqueous layers are filtered, acidified with concentrated HCl, and filtered; and the collected solid washed with water, thereby producing p-fluoro-α-methylcinnamic acid which is used as obtained.

(B) p-Fluoro-α-methylhydrocinnamic acid.

To p-fluoro-α-methylcinnamic acid (177.9 g., 0.987 mole) in 3.6 l. ethanol is added 11.0 g. of 5% Pd/C and the mixture is reduced at room temperature under a hydrogen pressure of 40 p.s.i. uptake is 31/32 lbs. (97% of theoretical). After the catalyst is filtered, the filtrate is concentrated in vacuo to give the product, p-fluoro-α-methylhydrocinnamic acid that is used without weighing in next step.

(C) 6-Fluoro-2-methylindanone.

To polyphosphoric acid (932 g ) at 70° C. on the steam bath is added p-fluoro-α-methylhydrocinnamic acid (93.2 g., 0.5 mole) slowly with stirring. The temperature is gradually raised to 95° C., and the mixture is kept at that temperature for 1 hour. The mixture is allowed to cool and added to 2 l. of water. The aqueous layer is extracted with ether, the ether solution washed twice with saturated sodium chloride solution, 5% $Na_2CO_3$ solution, water, and then dried. The ether filtrate is concentrated with 200 g. silica-gel, and added to a five pound silica-gel column packed with 5% ether-petroleum ether. The column is eluted with 5–10% ether-petroleum ether and followed by TLC to give 6-fluoro-2-methylindanone.

(D) 5-fluoro-2-methylindanone-3-acetic acid.

A mixture of 6-fluoro-2-methylindanone (18.4 g., 0.112 g. mole), cyanoacetic acid (10.5 g., 0.123 mole), acetic acid (6.6 g.), and ammonium acetate (1.7 g.) in dry toluene (15.5 ml.) is refluxed with stirring for 21 hours, as the liberated water is collected in a Dean Stark trap. The toluene is concentrated, and the residue dissolved in 60 ml of hot ethanol and 14 ml. of 2.2N aqueous potassium hydroxide solution. 22 g. of 8.5% KOH in 150 ml of water is added, and the mixture refluxed for 13 hours under nitrogen. The ethanol is removed under vacuum, water (500 ml) is added; and the aqueous solution washed well with ether and then boiled with charcoal. The aqueous filtrate is acidified to pH 2 with 50% hydrochloric acid, cooled and the precipitate collected. In this way dried 5-fluoro-2-methylindenyl-3-acetic acid (M.P. 164–166° C.) is obtained.

(E) 5-fluoro-2-methyl-1-(p-methylthiobenzylidene)-3-indenyl acetic acid.

5-fluoro-2-methyl-3-indenyl acetic acid (15 g., 0.072 mole) p-methylthiobenzaldehyde (14.0 g., 0.091 mole) and sodium methoxide (13.0 g., 0.24 mole) are heated in methanol (200 ml.) at 60 degree(s) under nitrogen with stirring for 6 hours. After cooling, the reaction mixture is poured into ice-water (750 ml), acidified with 2.5N hydrochloric acid, and the collected solid triturated with a little ether to produce 5-fluoro-2-methyl-1-(p-methylthiobenzylidene)-3-indenyl acetic acid (M.P. 187–188.2° C.). U.V. in methanol λmax. 348 mμ (E % 500), 258 (557), 258 (495), 353 (513), 262.5 (577), 242.5. (511).

(F) 5-fluoro-2-methyl-1-(p-methylsulfinylbenzylidene)-3-indenyl acetic acid.

To a solution of 5-fluoro-2-methyl-1-(p-methylthiobenzylidene)-3-indenyl acetic acid (3.4 g., 0.01 mole) in a mixture of methanol (250 ml.) and acetone (100 ml.) is added a solution of sodium periodate (3.8 g., 0.018 mole) in water (50 ml.) with stirring. Water (450 ml.) is added after 18 hours, and the organic solvents removed under vacuum below 30° C. The precipitated product is filtered, dried and recrystallized from ethyl acetate to give 5-fluoro-2-methyl-1-(rho-methylsulfinylbenzylidene)-3-indenyl acetic acid. Upon repeated recrystallization upon ethylacetate there is obtained cis-5-fluoro-2-methyl-1-(p-methylsulfinylbenzylidene)-3-indenyl acetic acid, M.P. 184–186° C. U.V. in methanol; λmax 328 (E % 377), 286 (432), 257.5 shldr. (413), 227 (548). Further runs reveal the existence of a second polymorph of cis-5-fluoro-2-methyl-1-(p-methylsulfinylbenzylidene)-3-indenyl acetic acid, M.P. 179–181° C. 5-Chloro-2-methyl-1-(p-methylsulfinylbenzylidene)-3-indenyl acetic acid is prepared by the procedure as described previously in this Example, and can be converted to the corresponding sulfonyl compound by the procedure set forth below.

5-fluoro-2-methyl-1-(p-methylsulfonylbenzylidene)-3-indenyl acetic acid is prepared by adding sodium methoxide (4.4M in MeOH, 68.5 ml, 0.3 mol) dropwise to a stirred, cooled mixture of 5-fluoro-2-methyl-1-(p-methylsulfinylbenzylidene)-3-indenyl acetic acid (100 g, 0.281 mol) in methanol (250 ml) and acetonitrile (500 ml). Sodium bicarbonate (0.56 mol) and hydrogen peroxide (30% in water, 0.56 mol) are added and allowed to react for 18 hours at −10° C. Excess sodium bicarbonate is filtered off, and cooled filtrate (0° C.) neutralized dropwise to pH 7 with 1M hydrochloric acid (350 ml). The resulting product is then filtered and washed with methanol. A thin layer chromatography system to check for purity utilizes chloroform:methyl isobutyl ketone (8:2); the $R_f$ value is 0.21. A tetrahydrofuran/diisopropyl ether combination can be used for product recrystallization. Reaction yield is 89%. ($R_1$=5-fluoro; $R_2$=$CH_3$; $R_3$=hydrogen; $R_4$=COOH; $R_5$=$CH_3$ $SO_2$; n=1).

Formula: $C_{20}H_{17}FO_4S$; Molecular Mass: 372.41 g/mol; Melting point: 204–206° C.; $^1$H-NMR [ppm] (DMSO-$d_6$): 2.16 (s,3, —$CH_3$); 3.30 (s,3,—$SO_2$—$CH_3$); 3.59 (s,2,—$CH_2$—C=O);6.70–7.17 (m,3,ar.); 7.38 (s,1,=CH—); 7.78–8.04 (AB,4,—Ph—$SO_2$—); HPLC (C-18 Column, 50% acetic acid (2%)/50% acetonitrile, 1.5 ml/min):

IR [cm$^{-1}$] (KBr): 1710 C=O; 1310 S=O; 1180 C—F; 1140 S=O;

α-[1-(p-Methylsulfonylbenzylidene)-2-methyl-5-fluoro-3-indenyl]-propionic acid is prepared by the similar procedures known in the art.

EXAMPLE 2

α-(1-p-Methylsulfonylbenzylidene)-2-Methyl-5-Fluoro-3-Indeny-1-Acetic Acid Methyl Ester 5-Fluoro-2-methyl-1-(p-methylsulfonylbenzylidene)-3-indenyl acetic acid is prepared by the procedure of Example 1, and converted to the methyl ester derivative by the following procedure. Sodium methoxide (4.4M in methanol, 1.36 ml, 0.006 mol) is added to a stirred cooled solution (0 degree(s) C.) of 5-fluoro-2-methyl-1-(p-methylsulfonylbenzylidene)-3-indenyl acetic acid (1.04 g, 0.0028 mol) in methanol (5 ml) and acetonitrile (10 ml). After 30 minutes, the reaction mixture is dropped into concentrated hydrochloric acid (50 ml) and extracted with methylene chloride (3×25 ml). The organic layer is extracted with saturated sodium bicarbonate (3×25 ml), dried with sodium sulfate, and concentrated in vacuo. The resulting oil is crystallized from tetrahydrofuran/hexane to yield 0.2 g of the desired compound. The melting point is 165–166° C. ($R_1$=5-fluoro; $R_2$=$CH_3$; $R_3$=hydrogen; $R_4$=COO $CH_3$; $R_5$=$CH_3$ $SO_2$; n=1). Other methyl esters of compounds useful in this invention can be prepared in a similar fashion.

EXAMPLE 3

(Z)-5-Fluoro-2-Methyl-1-(4-Methylsulfonylbenzylidene)-1H-3-Indenyl-(2-Hydroxy) Ethane (A) Methyl-5-fluoro-2-methyl-1H-3-indenylacetate Nitrosomethylurea (99.5 mmol) is added in portions to a cold (0° C.) mixture of aqueous 50% KOH (50 ml) and diethylether (150 ml) at 0° C. The yellow ether solution of diazomethane (Note: explosive) is separated, is washed with water, and is added in portions to a solution of 5-fluoro-2-methylindene-3-acetic acid (90 mmol) in dichloromethane (200 ml). When the evolution of $N_2$ ceases, the reaction is complete. After evaporation of the solvents, the residue is recrystallized from hexane to give methyl 5-fluoro-2-methyl-3-indenylacetate (yield 93%; m.p. 53° C.).

(B) 5-Fluoro-2-methyl-1H-3-indenyl-(2-hydroxy) ethane

To a solution of methyl 5-fluoro-2-methyl-3-indenylacetate (24 g) in dry THF (300 ml) lithiumaluminum hydride (6.9 g) is added. The mixture is stirred at room temperature for 1.5 hours. Excess LiAlH$_4$ is destroyed with saturated aqueous NaHSO$_4$ solution. The organic phase is concentrated in vacuo, and the crude product is purified via silica gel column chromatography elution with methylene chloride. The residue is recrystallized from hexane to give 5-fluoro-2-methyl-1H-3-indenyl-(2-hydroxy) ethane (yield 63%; m.p. 65°–66.5° C.).

(C) (Z)-5-Fluoro-2-Methyl-1-(4-Methylsulfonylbenzylidene)-1H-3-Indenyl-(2-Hydroxy) Ethane 5-Fluoro-2-methyl-1H-3-indenyl-(2-hydroxy) ethane (15 g, 0.072 mol) p-methylsulfonylbenzaldehyde (14.0 g, 0.091 mol) and sodium methoxide (13.0 g, 0.24 mol) are heated in methanol (200 ml) at 60° C. under nitrogen with stirring for 6 hours. The reaction mixture is poured onto ice-water (750 g), and is acidified with 2.5N hydrochloric acid. The collected solid is triturated with a little ether to produce (Z)-5-fluoro-2-methyl-1-(p-methylsulfonylbenzylidene)-1H-3-indenyl-(2-hydroxy) ethane. Recrystallization of the crude reaction product results in the separation of the mixture of geometrical isomers (Z/E) and gives the title compound (R$_1$=5-fluoro, R$_2$=CH$_3$, R$_3$=H, R$_4$=CH$_2$OH, n=1, R$_5$=CH$_3$ SO$_2$).

Formula: C$_{20}$H$_{19}$FO$_3$S; Molecular Mass: 358.43 g/mol; Melting point: 118° C.; $^1$H-NMR [ppm] (DMSO-d$_6$): 2.14 (s,3,—CH$_3$); 2.71 (t,2,—CH$_2$—); 3.29 (s,3,—SO$_2$—CH$_3$); 3.55 (m,3,—CH$_2$—O); 4.70 (m,1,—OH); 6.68–7.14 (m,3, ar.);7.30 (s,1,=CH); 7.76–8.03 (AB,4,—Ph—SO$_2$—); IR [cm$^{-1}$] (KBr): 3440 OH; 1300 S=O; 1170 C—F; 1140 S=O Examples 4-5 illustrate preparation of oral and intraveneous formulations incorporating the compounds above.

EXAMPLE 4

CAPSULE FORMULATIONS

The table below shows the composition of 150 mg (A) and 100 mg (B) capsules containing the compound of Example 1.

| FORMULATION | A | B |
| --- | --- | --- |
| Example 1 Compound | 150 mg | 100 mg |
| Lactose Monohydrate, NF | 207 mg | 138 mg |
| Corscarmellose Sodium, NF | 15 mg | 10 mg |
| Colloidal Silicon Dioxide, NF | 1 mg | 0.7 mg |
| Magnesium Stearate, NF | 6.3 mg | 4.2 mg |
| Sodium Lauryl Sulfate, NF | 0.7 mg | 0.5 mg |
| Gelatin Capsule Size & Color | #1, Yellow | #2, Yellow or Natural |

EXAMPLE 5

Formulation for Sterile Intravenous Injection

| | Amount (grams/Liter) |
| --- | --- |
| Compound of Example 1 | 0.01–10 |
| Sodium chloride | 13.04 |
| Potassium chloride | 0.712 |
| Sodium chloride (monobasic) | 0.206 |
| Sodium bicarbonate | 4.908 |
| Calcium chloride | 0.306 |
| Magnesium chloride | 0.318 |
| Dextrose | 1.8 |
| NaOH/HCl | qs to pH 7.4 |
| Hydroxypropylcyclodextran | 0.1–1% (as a carrier) |

BIOLOGICAL EFFECTS

Pulmonary fibrosis is characterized by an inflammatory alveolitis associated with granuloma formation that can progress to fibrosis of the lung. Recent studies have indicated that abnormal neovascularization, or angiogenesis, is a driving forces responsible for the progression of pulmonary sarcoidosis. For example, bronchoalveolar lavage (BAL) cells from pulmonary sarcoidosis patients will elicit an angiogenic response following subcutaneuous injection. The basis for this effect may be related to the ability of the cells to release pro-angiogenic cytokines such as VEGF, bFGF, or IL-8 since cell homogenate are also capable of eliciting the response. This activity correlated with the chronic inflammatory response. Nonsteroidal anti-inflammatory drugs are contraindicated for this effects since inhibition of cyclooxygenase and reduction of prostaglandin content causes vasoconstriction. The invention describes an unexpected finding which involves a sulfone metabolite of the NSAID, sulindac, which lacks cycooxygenase inhibitory activity. The sulfone was discovered to inhibit new blood vessel formation in the mouse cutaneous angiogenesis assay as described previously by Sidky and Auerbach. The results showing a strong anti-angiogenic effect for BAL cells from sarcoidosis patients indicate a benefit of sulfone and related analogs for sarcoidosis without contraindications involving depletion of prostaglandin levels.

It will be understood that various changes and modifications may be made in the details of procedure, formulation and use without departing from the spirit of the invention, especially as defined in the following claims.

We claim:

1. A method for treating a patient with sarcoidosis, comprising administering to the patient a physiologically effective amount of a compound of the formula:

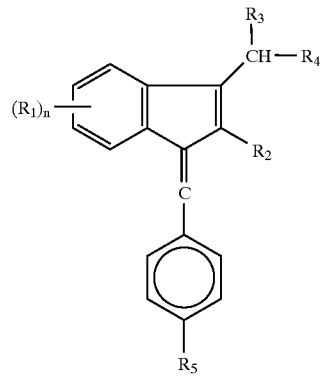

wherein R$_1$ is independently selected in each instance from the group consisting of hydrogen, halogen, lower alkoxy, hydroxy, lower alkyl, lower alkyl mercapto, lower alkylsulfonyl, lower alkylamino, di-lower alkyl amino, amino, nitro, nitrile, lower alkyl carboxylate, —CO$_2$H, and sulfonamido;

$R_2$ is selected from the group consisting of hydrogen and lower alkyl;

$R_3$ is selected from the group consisting of hydrogen, lower alkyl, hydroxy, and amino;

$R_4$ is selected from the group consisting of —COM and $CH_2OH$ wherein M is selected from the group consisting of hydroxy, substituted lower alkoxy, amino, alkylamino, dialkylamino, N-morpholino, hydroxyalkylamino, polyhydroxyamino, dialkylaminoalkylamino, aminoalklyamino, and the group OMe, wherein Me is a cation;

$R_5$ is an alkyl sulfonyl; and n is an integer from 0 to four.

2. The method of claim 1 wherein $R_1$ is halogen and n is 1.

3. The method of claim 2 wherein $R_1$ is 5-fluoro.

4. The method of claim 2 wherein $R_2$ is lower alkyl.

5. The method of claim 4 wherein $R_2$ is methyl.

6. The method of claim 4 wherein M is hydroxy; and $R_3$ is selected from the group consisting of hydrogen or lower alkyl.

7. The method of claim 6 wherein $R_3$ is hydrogen.

* * * * *